United States Patent
Stibrany et al.

(12) 
(10) Patent No.: US 6,501,000 B1
(45) Date of Patent: Dec. 31, 2002

(54) LATE TRANSITION METAL CATALYST COMPLEXES AND OLIGOMERS THEREFROM

(75) Inventors: Robert Timothy Stibrany, Long Valley; Michael Gerard Matturro, Lambertville; Stephen Zushma, Clinton; Abhimanyu Onkar Patil, Westfield, all of NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 09/542,892

(22) Filed: Apr. 4, 2000

(51) Int. Cl.[7] .............................. C07C 2/26; C07C 2/34; B01J 31/00; B01J 31/18

(52) U.S. Cl. ..................... 585/511; 585/520; 585/521; 585/527; 502/155; 502/167; 502/171; 502/152

(58) Field of Search .................................. 502/155, 167, 502/171, 152; 585/511, 520, 521, 527

(56) References Cited

U.S. PATENT DOCUMENTS

| | | | |
|---|---|---|---|
| 3,179,649 A | 4/1965 | Feay et al. | 260/94.9 |
| 3,506,597 A | 4/1970 | Asai et al. | 260/2 |
| 3,546,083 A | 12/1970 | Ort et al. | 204/131 |
| 3,558,520 A | 1/1971 | Kubicek et al. | 252/429 |
| 3,703,561 A | 11/1972 | Kubicek et al. | 260/683 D |
| 3,954,664 A | 5/1976 | Napier et al. | 252/429 R |
| 4,471,068 A | 9/1984 | Haitko | 502/165 |
| 4,477,589 A | 10/1984 | van der Hulst et al. | 502/169 |
| 4,668,838 A | 5/1987 | Briggs | 585/513 |
| 4,740,644 A | 4/1988 | Eichhorn et al. | 570/245 |
| 4,777,315 A | 10/1988 | Levin et al. | 585/512 |
| 5,068,310 A | 11/1991 | Shaffer | 528/215 |
| 5,198,401 A | 3/1993 | Turner et al. | 502/155 |
| 5,266,665 A | 11/1993 | Hardiman | 526/117 |
| 5,316,994 A | 5/1994 | Kelsey | 502/117 |
| 5,369,073 A | 11/1994 | Sommazzi et al. | 502/162 |
| 5,434,117 A | 7/1995 | Klusener et al. | 502/162 |
| 5,494,874 A | 2/1996 | Rosen et al. | 502/155 |
| 5,550,305 A | 8/1996 | Wu | 585/513 |
| 5,554,704 A | 9/1996 | Burkhardt et al. | 526/153 |
| 5,556,823 A | 9/1996 | Sommazi | 502/162 |
| 5,707,913 A | 1/1998 | Schlund et al. | 502/102 |
| 5,750,455 A | 5/1998 | Chauvin et al. | 502/164 |
| 5,763,723 A | 6/1998 | Reagan et al. | 585/513 |
| 5,824,711 A | 10/1998 | Kimock et al. | 521/129 |
| 5,841,013 A | 11/1998 | Ho et al. | 585/269 |
| 5,863,853 A | 1/1999 | Vaughan et al. | 502/108 |
| 5,866,663 A | 2/1999 | Brookhart et al. | 526/170 |
| 5,886,224 A | 3/1999 | Brookhart et al. | 564/272 |
| 5,916,989 A | 6/1999 | Brookhart et al. | 526/348.6 |
| 5,972,823 A | 10/1999 | Walzer, jr. | 502/152 |
| 6,034,259 A | 3/2000 | Brookhart et al. | 556/137 |
| 6,037,297 A | 3/2000 | Stibrany et al. | 502/155 |
| 6,174,976 B1 * | 1/2001 | Killian et al. | 526/172 |
| 6,200,925 B1 * | 3/2001 | Ponasik, Jr. et al. | 502/162 |

FOREIGN PATENT DOCUMENTS

| | | |
|---|---|---|
| AU | 222414 | 1/1958 |
| DE | 1520876 | 7/1964 |
| DE | 2060378 | 12/1970 |
| EP | 0560455 A1 | 9/1993 |
| EP | 0560456 A1 | 9/1993 |
| GB | 832319 | 4/1960 |
| JP | 634196 | 4/1963 |
| JP | 55094329 | 7/1980 |
| JP | 56022751 | 3/1981 |
| JP | 57038733 | 3/1982 |
| JP | 63159362 A | 7/1988 |
| JP | 03275063 A | 12/1991 |
| JP | 54039032 | 3/1997 |
| JP | 10298231 | 11/1998 |
| WO | WO9623010 | 8/1996 |
| WO | WO9640805 | 12/1996 |
| WO | WO978736 | 12/1997 |
| WO | WO9930822 | 6/1999 |

OTHER PUBLICATIONS

"Steric Effects on Complex Formation between Nickel(II) and (2–imidazoleazo)besene, 2,2'–biimidazole and 2,2'–bibenzimidazole" Anadi C. Dash, Achuta N. Acharya, Ramakanta Sahoo; Transition met. Chem., 21, pp. 337–344 (1996).

"Fluctuations between Square–Planar and Tetrahedral Coordination Geometry with bis(2–benzimidazolyl)alkane Ligands. Synthesis, Spectroscopic Properties and X–ray Crystal Structure of Four Representative Examples"; Gerard A. van Albada, Wilberth J. J. Smeets, Nora Veldman, Anthony L. Spek, Jan Reedijk; Inorganica Chimica Acta 290 (1999), pp. 105–112.

"Cobalt(II), Nickel(II) and Copper(II) Complexes of Bidentate Binezimidazoles"; Malatesh A. Pujar and Timmanagood D. Bharamgoodar; Transition Met. Chem., 13, pp. 423–425 (1988).

"Tetrahedral Coordination by a Seven–Membered Chelate Ring"; Vanessa Broughton, Gérald Bernardinelli, Alan F. Williams; Inorganica Chimica Acta, pp. 275–276 (1998) pp. 279–188.

(List continued on next page.)

Primary Examiner—Walter D. Griffin
(74) Attorney, Agent, or Firm—Joseph C. Wang

(57) ABSTRACT

The invention is directed towards a composition comprising the formula $LMX(X')_n$ wherein n equals 0 or 1; X and X' are independently selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolates, carbon monoxide, cyanate, olefins, and any other moiety into which a monomer can insert; M is selected from the group consisting of nickel, palladium, and platinum and L is a nitrogen-containing bidentate ligand with more than two nitrogen atoms. The composition possesses a tetrahedral or pseudo-tetrahedral structure. The invention also provides a method for using the composition in conjunction with an activating cocatalyst to form short chain α-olefins.

20 Claims, 1 Drawing Sheet

OTHER PUBLICATIONS

"A Novel Type of Tetranuclear Cluster with the Trinucleating Ligand 1,2–Bis(benzimidazol-2-yl)-1-hydroxyethane. Crystal and Molecular Structure of $Ni(HRSL)_2(CF_3SI_3)_2$ and $[CU_4(SL)_4(NO_3)_2(EtOH)](NO_3O_2(EtOH)_3(HO_2)$; Spectroscopy and Magnestism of these and Related transition metal Compounds"; Gerard A. van Albada, Jan Reedijk, Reijo Hämäläinen, Urtho Turpeinen, and Anthony L. Spek; Inorganica Chimica Acta, 163 (1989), pp. 213–222.

"Synthesis X–ray Crystal Structure and Magnetism of $[NiCl_2\{(bis(2-benzimidazolyl)propane\}]_2 \cdot (C_2H_5OH)_2$—A Second Example of Ferromagnetically Coupled Five–Coordinated High–Spin Dichloro–Bridged Nickel(II) Dimer"; Gerard A. van Albada, Jeroen J. A. Kolnaar, Wilberth J. J. Smeets, Anthony L. Spek and John Reedijk; Eur. J. Inorg. Chem. 1998, pp. 1337–1341.

"Exchange Interactions, Charge Delocaliztion and Spin Relaxation in a Mixed–Valence Di–iron Complex Studied by Mossbauer Spectroscopy", X.–Q ding, E. Bill, A. X. Trautwein, and H. Winkler, A. Kostikas, V. Papaefthymiou, and A. Simpoulos, P. Beardwood and J. F. Gibson; J. Chem. Phys. 99 (9), Nov. 1, 1993, pp. 6421–6428.

Iron–Sulfur Dimers with Benzimidazole–Thiolate,-Phenolate or Bis(benzimidazolate) Terminal Chelating Ligands. Models for Rieske–type Proteins; Peter Beardwood and John F. Gibson; J. CHem. Soc. Dalton Trans. 1992; pp. 2457–2446.

"Iron–Sulfur Dimers with Benzimidazolat–Thiolate, Benzimidazolate–Phenolate, or Bis(benzimidazolate) Terminal Chelating Ligands"; Peter Beardwood and John F. Gibson; J. Chem. Soc., Chem. Commun., 1986, pp. 490–492.

"A Mössbauer and Electrochemical Study of Mononuclear Iron(III) Complexes with Benzimidazole–based Flexible Bidentate Ligands"; Veena Arora, Rajesh, and Pavan Mathur, Sampat R. Vadera; Transition met. Chem., 24, pp. 92–94 (1999).

$[6,6'-Bis(benzimidazol-2-yl-N^3)-2,2'=bi-pyridine]$dichlorocobalt(II)–Dimethylform–amide (½); K.–L. Cheng, S.–C. Sheu, G.–H. Lee, Y.–C,. Lin, Y. Wang and T.–I. Ho; Acta Crystallographica Section C., Cryst. Struct. Commun. (1997), C53(9), pp. 1238–1240.

Binuclear Complexes of Ruthenium and Osmium Bridged by 2,2'–Bibenzimidazolate: Preparation, Electrochemistry, and Formation of Mixed–Valence Complexes; Masaaki Haga, Takeko Matsumura–Inoue, and Shinichi Yamabe; Inorg. Chem. 1987, 26, pp. 4148–4154.

"Synthesis, Characterisation, Antifungal and Antibacterial Studies of Nickel(II) and Silver(I) Complexes of Tridenate Bis Benzimidazoles"; P.C. Vyas and Navneet Kaur; Asian Journal of Chemistry; vol. 9, No. 2 (1997), pp. 208–212.

"Synthesis and Characterization of 2,2'–Bibenzenimidazole and its Metal Complex"; Lai, Chien Hsien; Chern, Shuenn Shing; Peng, Shie–Ming; Bull. Inst. Chem., Academia. Sinica (1988), vol. 35, pp. 31–44.

"Complexes of Copper(II), Cobalt(II) and Nickel(II) with Substituted Benzimidazoles"; Donappa, N.; Naikar, S. B.; Asian Journal of Chem. (1993), vol. 5, No. 4, pp. 995–1000.

"Studies on Benzenesulfonamidomethylbenzimidazoles. Part IX: Acid Dissociation Constants of Nickel(II) Complexes of 1–Benzenesulfonamido–1,2–bis(2'–benzimidazolyl)ethane"; Ghosh, N. N.; Nandi, M. M.; J. Indian Chem. Soc. vol. L V, Aug. (1978), 55(8), pp. 749–751.

"Studies on Benzenesulfonamidomethylbenzimidazoles. Part VII. Copper(II), Cobalt(II) and Nickel(II) Chelates of Benzenesulfonamido–ethylene–2,2'–dibenzimidazole"; Ghosh, N. N.; Nandi, M. M.; J. Indian Chem. Soc., Vol. L V. Jan., Feb., Mar. (1977), 54(1–3), pp. 139–142.

Chauvin et al., "Catalytic Dimerization of Propene by Nickel–Phosphine Complexes in 1–Butyl–3–methylimidazolium Chloride/$AlEt_xCl_{3-x}$(X=0,1) Ionic Liquids", Institut Francais du Petrole, Rueil–Malmaison, France, 1995, pp. 1149–1155.

Rogers et al., "Ethoxyboratabenzene Zirconium Complexes: Catalysts for α–Olefin Production", Dept. of Chemistry, Univ. of Rochester, New York, Jun. 16, 1997, pp. 9305–9306.

Yang et al., "Cation–like" Homogeneous Olefin Polymerization Catalysts Based Upon Zirconocene Alkyls and Tris(pentafluorophenyl)borane, Dept. of Chemistry, Northwestern Univ., Evanston, Il, Dec. 17, 1990.

Einloft et al., "Selective Two–Phase Catalytic Ethylene Dimerization by $Ni^{II}$ Complexes/$AlEtCl_2$ Dissolved in Organoaluminate Ionic Liquids", Polyhedron, vol. 15, No. 19, Jan. 16, 1996, pp. 3257–3259.

Chandra et al., "Preparation of $\eta^5$ –cyclopentadienyltitanium trichloride and $\eta^5$ –methylcyclopentadienyltitanium trichloride", Dept. of Chemistry, Univ. of Delhi, India, Oct. 15, 1979.

Bhalla et al, "Synthesis and Coordination Chemistry of the Bis(imidazole) Ligand, Bis(1–methyl–4,5–diphenylimidaz–2–oyl)(benzyloxy)methane", Chemistry Dept. Univ of Manchester, England, Oct. 2, 1996, pp. 2944–2949.

Knapp et al, "Preparation, Structure, and Properties of Pseudotetrahedral, $D_{2d}$ Complexes of CU(II), Ni(II), Co(II), Cu(I), and Zn(II) with the Geometrically Constraining Bidentate Ligand 2,2'Bis(2–imidazolyl)biphenyl. Examination of Electron Self–Exchange for theCU(I)/Cu(II) Pair", Dept. of Chemistry, Rutgers Univ., New Brunswick, New Jersey, Sep. 5, 1989, pp. 3452–3463.

* cited by examiner

LATE TRANSITION METAL CATALYST COMPLEXES AND OLIGOMERS THEREFROM

FIELD OF THE INVENTION

The invention is directed towards a pseudotetrahedral late transition metal catalyst complex and its use in forming α-olefins.

BACKGROUND

The chemical industry uses α-olefins as intermediates in a variety of processes. In particular, linear α-olefins are used in the formation of polyolefins such as ethylene butylene copolymers. Other products formed from α-olefins include surfactants, lubricants and plasticizers. Paraffin wax cracking, paraffin dehydrogenation and alcohol dehydration processes can be used to produce α-olefins; however, most of the short chain linear α-olefins currently used in the chemical industry are produced by ethylene oligomerization. Ethylene oligomerization is a desirable route due to the availability and low cost of ethylene. Additionally, the product quality is also acceptable for most applications.

In recent years, the chemical industry has employed the use of organometallic catalysts to produce polymers. While many advances in organometallic catalyst technology have been made, researchers continue to seek superior catalyst compositions. In fact, very recently, novel late transition organometallic catalysts have been discovered which are very effectively used in polymerization processes. More specifically, U.S. Pat. No. 6,037,297 to Stibrany et al., herein incorporated by reference, details group IB (Cu, Ag and Au) containing catalyst compositions that are useful in polymerization processes.

Organometallic catalyst technology is also a viable tool in oligomerization processes which produce linear α-olefins for use as feedstock in various other processes. However, one problem often encountered when using many of these catalyst systems is the propensity to produce α-olefins with very low selectivity (i.e., a Schulz-Flory type distribution with high k values). For instance, many of the linear α-olefins made today utilize a neutral nickel (II) catalyst having a planar geometry and containing bidentate monoanionic ligands. While these planar nickel (II) catalysts do produce linear α-olefins, these catalysis systems exhibit a Schulz-Flory type of distribution over a very wide range (i.e., $C_4$–$C_{30+}$).

To address Schulz-Flory distribution problem, chromium metal based catalysts have become popular for use in certain oligomerization processes. More precisely, chromium complexes have been used to oligomerize ethylene in order to form linear α-olefins with improved distributions. In fact, there has been a report of a specific chromium catalyst which selectively trimerizes ethylene to 1-hexene. These techniques employ the use of a chromium compound in conjunction with aluminoxane along with one of a variety of compounds such as nitrites, amines and ethers. Unfortunately, while these techniques have been able to selectively produce α-olefins, polymer is formed as a co-product. Of course, when polymer is co-produced, the yield of desirable product decreases accordingly. Also, as a practical matter, polymer build-up in the reaction vessel can severely hamper production efficiency thereby limiting the commercial use of such processes.

As discussed above, the organometallic catalyst technology now being used to produce α-olefins has two major disadvantages. First, many of the organometallic catalysts produce α-olefins with a Schulz-Flory type distribution. Unfortunately this Schulz-Flory type distribution is not ideal when short chain α-olefins are desired—in other words, the selectivity is not good enough to maintain efficient processes. Because α-olefins are used as inter-mediates for specific products, α-olefins with certain chain lengths are desired. For instance, the following are examples of α-olefin chain lengths that would be desirable as feeds for certain product types: $C_4$ to $C_8$ for comonomer in ethylene polymerization; $C_{10}$ for lube quality poly-α-olefins; and $C_{12}$ to $C_{20}$ for surfactant products. Thus, considerable inefficiency and waste is present when significant amounts of α-olefins produced having chain lengths outside of the range required for production of a particular chemical. Second, while some of the current organometallic catalysts may improve selectivity, most also produce polymer co-product. This lowers the yield of desired product and can also accumulate in the reaction vessel—both of which make commercial use less attractive and inefficient. Hence, there is still a need for improving the selectively and efficiency of linear α-olefin production.

SUMMARY

The instant invention provides a late transition metal catalyst composition having a pseudotetrahedral geometric structure and its use in forming α-olefins. The instant invention can be used to selectively produce short chain α-olefins without producing a significant percentage of polymer co-product. Thus, the two problems noted above with regard to current oligomerization processes are overcome.

In one embodiment, the invention is a composition having the formula $LMX(X')_n$ wherein n equals 0 or 1; X and X' are independently selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolates, carbon monoxide, cyanate, olefins, and any other moiety into which a monomer can insert; M is selected from the group consisting of nickel, palladium, and platinum and L is a nitrogen-containing bidentate ligand with more than two nitrogen atoms.

In another embodiment, the invention is a catalyst composition comprising the reaction product of a composition having the formula $LMX(X')_n$, as described above, and an activating cocatalyst. This embodiment of the invention is particularly useful in oligomerization chemistry.

Also provided for is a method for selectively and efficiently producing short chain linear α-olefins. The method includes contacting olefinic monomers under oligomerization conditions with a catalyst composition comprising a composition having the formula $LMX(X')_n$, as defined above, and an activating cocatalyst.

These and other features, aspects and advantages of the present invention will become better understood with regard to the following description, appended claims, and accompanying FIGURE.

BRIEF DESCRIPTION OF DRAWING

The FIGURE shows one embodiment of the pseudotetrahedral crystal structure of 2,2'-bis[2-(1-ethylbenzimidazol-2yl)]biphenyl]nickel(II) dichloride (hereinafter a.k.a., Ni(diEtBBIL)Cl$_2$).

DETAILED DESCRIPTION

Figure 1:
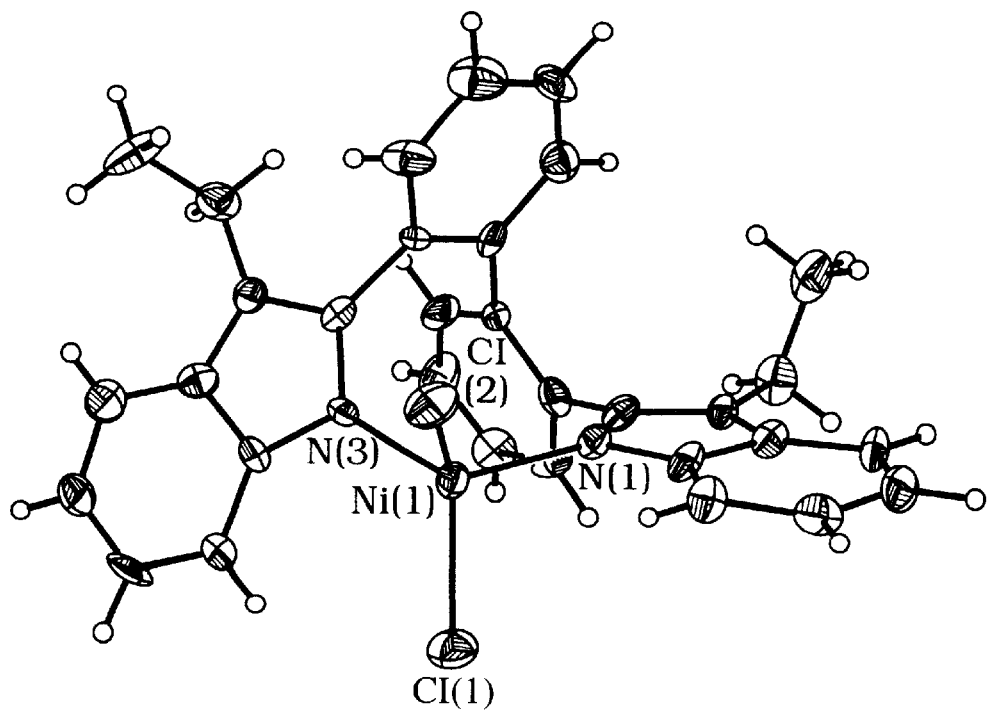

The invention relates to a novel pseudotetrahedral metal complex which, when used with an activating cocatalyst, provides a novel catalyst composition. The invention also provides a novel oligomerization method which utilizes the catalyst composition. Generally speaking, the method of the invention selectively produces oligomers. The term "oligomers" as used in this specification should be appreciated by one skilled in the art as meaning a α-olefin having approximately three to forty carbon atoms. More preferred "short chain" linear α-olefins have approximately three to twelve carbon atoms. Most preferred short chain linear α-olefins have approximately four to ten carbon atoms. Further, the olefinic monomers used to produce the linear α-olefins are defined as short chain linear olefins such as ethylene, propylene and butene. Longer chain olefinic monomers such as hexene and octene may also be employed to produce the linear α-olefins. It should also be appreciated by those skilled in the art that although the term "pseudotetrahedral" is used to describe the geometric structure of the metal complex, it does not exclude a pure "tetrahedral" geometrical arrangement. The prefix "pseudo" is used throughout the specification to most accurately describe the non-limiting embodiments described herein.

More specifically, the invention is based upon the reaction of a group VIIIA metal complex having a bidentate nitrogen ligand with a pseudotetrahedral arrangement around the metal (e.g., Ni, Pd or Pt), with and activating cocatalyst such as methyl alumoxane (a.k.a., "MAO"). Furthermore, by controlling the temperature, catalyst loading, ligand structure, and residence time, product selectivity can be adjusted to produce individual α-olefins such as 1-butene with high selectivity (e.g., greater than 95%) or mixtures of linear or branched α-olefins in a narrow molecular weight range (e.g., $C_4$ to $C_8$ olefins).

The composition of this invention is a late transition metal complex having the formula $LMX(X')_n$ wherein n equals 0 or 1. X and X' are independently selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolates, carbon monoxide, cyanate, olefins including diolefins and cycloolefins, and any other moiety into which a monomer can insert. M is selected from the group consisting of nickel, palladium, and platinum. L is a nitrogen-containing bidentate ligand having more than two nitrogen atoms.

In a preferred embodiment, X and X' are independently selected from the group consisting chloride and bromide. In more preferred embodiment, X equals X'.

In another preferred embodiment L has the formula $A(ZR^*)_mA'$ or AA' wherein A and A' are independently selected from the group consisting of:

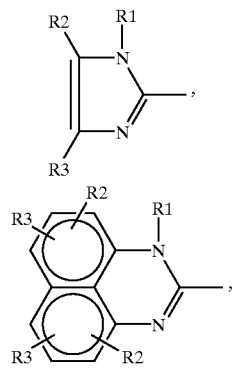

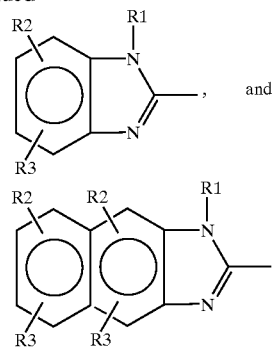

wherein R1 is independently selected from the group consisting of hydrogen, $C_1$ through $C_{12}$ alkyl, $C_3$ through $C_{12}$ cycloalkyl, aryl, and trifluoroethyl; R2 and R3 are independently selected from the group consisting of hydrogen, $C_1$ through $C_{12}$ alkyl, $C_3$ through $C_{12}$ cycloalkyl, $C_1$ through $C_{12}$ alkoxy, F, Cl, $SO_3$, $C_1$ through $C_{12}$ perfluoroalkyl, trimethylsilyl, and $N(CH_3)_2$. Z is carbon and R* is independently selected from the group consisting of hydrogen, $C_1$ through $C_{12}$ alkyl, $C_3$ through $C_{12}$ cyclo alkyl, aryl, $C_1$ through $C_{12}$ alkoxy, F, Cl, $SO_3$, $C_1$ through $C_{12}$ perfluoroalkyl, trimethylsilyl, and $N(CH_3)_2$. Finally, m equals an integer from 1 to 22. In a preferred embodiment, m equals 1 or 12.

Among the metal complexes of the present invention, those having the following ligands are particularly preferred: 1,1'-bis(1-methylbenzimidazol-2-yl)-1"-methoxymethane; 1,1'-bis(1-butylbenzimidazol-2yl)pentane; and 2,2'-bis(2-(1-ethylbenzimidazol-2-yl))biphenyl.

The 1,1'-bis(1-methylbenzimidazol-2-yl)-1"-methoxymethane ligand has the following structure:

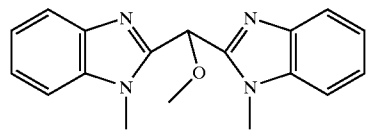

The 1,1'-bis(1-butylbenzimidazol-2yl)pentane ligand has the following structure:

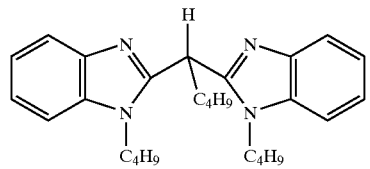

The 2,2'-bis(2-(1-ethylbenzimidazol-2-yl))biphenyl ligand has the following structure:

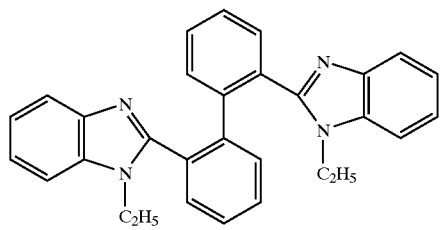

In another preferred embodiment, X and X' are independently selected from the group consisting of chloride and bromide. In a more preferred embodiment, X equals X'.

The invention also provides for the composition which is the reaction product of the composition having the formula $LMX(X')_n$, as defined above, and an activating cocatalyst. In one embodiment, the activating cocatalyst is selected from the group consisting of alkylalumoxanes, aluminum alkyls, aluminum halides, alkyl aluminum halides, Lewis acids, alkylating agents, and mixtures thereof. In a more preferred embodiment, the activating cocatalyst is methyl alumoxane. Finally, the preferred ratio of metal complex to activating cocatalyst is from $1:10^{-2}$ to $1:10^6$.

Lewis acids other than any of the foregoing list and the mixtures of the foregoing can also be used in conjunction with alkylating agents, such as methyl magnesium chloride and methyl lithium. Examples of such Lewis acids are those compounds corresponding to the formula: $R''''_3B$, where $R''''$ independently each occurrence is selected from hydrogen, silyl, hydrocarbyl, halohydrocarbyl, alkoxide, aryloxide, amide or combination thereof, said $R''''$ having up to 30 nonhydrogen atoms.

It is to be appreciated by those skilled in the art, that the above formula for the preferred Lewis acids represents an empirical formula, and that many Lewis acids exist as dimers or higher oligomers in solution or in the solid state. Other Lewis acids which are useful in the catalyst compositions of this invention will be apparent to those skilled in the art.

Other examples of suitable cocatalysts are discussed in U.S. patent application Ser. No. 09/212,035 filed Dec. 15, 1998 by Stibrany et al.; U.S. Pat. No. 5,198,401 and PCT patent documents PCT/US97/10418 and PCT/US96/09764, all incorporated by reference herein.

The composition described above may also be supported. The support material is preferably a porous material which includes, but is not limited to, inorganic oxides, talc, and inorganic chlorides. The support material may also be resinous materials such as polystyrene polyolefin or polymeric compounds. The support material may also be any other organic material that has an average particle size greater than approximately 10 micron. These catalysts are generally physisorbed on the support. The catalysts can also be supported on mesoporous materials. In a more preferred embodiment, the composition is supported by silica.

The novel composition of the invention can be used in conjunction with a cocatalyst to oligomerize olefinic monomers. Thus, the invention also provides a method for producing linear α-olefins by contacting olefinic monomers with the composition described above under certain temperature and pressure conditions conducive to forming oligomers while minimizing, or totally eliminating, any polymer co-product. Olefinic monomers used for producing the linear α-olefins include, but are not limited to, ethylene, propylene, butenes, and mixtures thereof. A preferred olefinic monomer is ethylene. In one embodiment, the invention produces linear α-olefins having approximately four to twenty carbon atoms. In a more preferred embodiment, the invention produces α-olefins having four to eight carbon atoms.

Generally, oligomerization may be accomplished utilizing similar temperatures and pressures used in the prior art. More specifically, temperature ranges from about –100 to 250° C. and at pressures from about 5 to 30000 psig are acceptable. The most preferred temperature range is from about 0° C. to 100° C. while the preferred is about 15 to 2000 psig.

Furthermore, oligomerization may take place in a solvent, neat (e.g., no solvent and liquid condensed olefin), or in a gas phase (e.g., olefin in gas phase and catalyst in the solid phase). When oligomerization is conducted in a solvent phase, suitable solvents include, but are not limited to, ethylene, propane, butane, pentane, hexane, toluene, methylene chloride, carbon dioxide and mixtures thereof.

As for oligomerization in a gas phase, Exxon Chemical's gas phase catalyst technology as described in U.S. Pat. No. 5,554,704 which is herein incorporated by reference. U.S. Pat. No. 5,554,704 teaches a process for producing a supported catalyst. The supported catalyst can then be used in a solvent free system wherein gas phase α-olefin is passed through a fixed bed of catalyst. The condensed α-olefin product is then separated from the system.

The bidentate ligands of the invention can be synthesized using techniques well known to those skilled in the art. See U.S. Pat. No. 6,037,297 to Stibrany et al., herein incorporated by reference, which explains how to synthesize bidentate ligands and also shows the structure of such ligands. The novel pseudotetrahedral metal complex can be synthesized by complexing a nickel, palladium or platinum compound with the ligands. This is most easily done by dissolving the nickel, palladium or platinum compound in a solvent then adding ligand and solvent. This mixture is then refluxed and cooled.

The invention is further described in the following non-limiting examples.

EXAMPLES

I. Catalyst Preparation

Example 1

Preparation of [1,1'-bis(1-methylbenzimidazol-2yl)1"methoxymethane]nickel(II) dibromide (a.k.a., "Ni(HBBIOMe)Br$_2$")

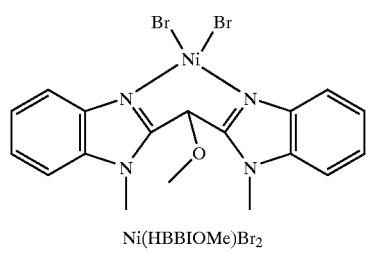

Ni(HBBIOMe)Br$_2$

A 100 mg (0.45 mmol) quantity of NiBr$_2$ was dissolved in 20 mL of ethanol to give a yellow solution. After the addition of 146 mg (0.46 mmol) of 1,1'bis(1-methylbenzimidazol-2yl)1"methoxymethane (prepared using tartronic acid 1,2 phenylenediamine with iodomethane as the alkylating agent as described in U.S. Pat. No. 6,037,297 to Stibrany et al., herein incorporated by reference) and the addition of 10 mL of toluene, the mixture was refluxed and stirred for 10 minutes. Upon cooling the mixture gave a pale-violet crystalline precipitate with a pale-green supernatant. The crystalline solid was collected by filtration and washed with about 10 ml of hexane. Upon drying in air 201 mg of pale-violet crystalline product was obtained (81.7% yield).

Example 2
Preparation of [1,1'bis(1-butylbenzimidazol-2yl)pentane] nickel(II) dichloride (a.k.a., "Ni(tributBBIM)Cl$_2$")

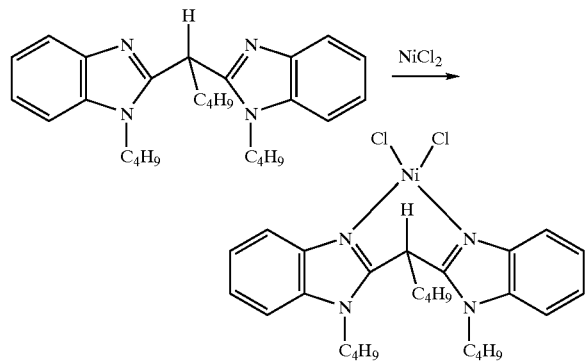

A 100 mg (0.42 mmol) quantity of NiCl$_2$·6H$_2$O was dissolved in 20 mL of absolute ethanol to give a yellow-green solution. Then 190 mg (0.46 mmol) of tributBBIM was added followed by the addition of 1 mL of triethylorthoformate. The solution was heated to gentle reflux for ca. 5 min. Upon cooling violet dichroic blades formed and 227 mg of solid was collected by filtration and washed with triethylformate followed by pentane. (98%), C$_{27}$H$_{36}$Cl$_2$N$_4$Ni, FW=546.22; mp 324–325° C. (decomp.); X-ray crystallographic data: monoclinic, a=14.0690 Å, b=14.1050 Å, c=14.3130 Å, α=90°, β=97.220°, γ=90°, V=2817.80 Å$^3$.

A 100 mg (0.42 mmol) quantity of NiCl$_2$·6H$_2$O was dissolved in a mixture consisting of 15 mL of ethanol and 1.5 mL of triethylorthoformate to give a yellow-green solution. After the addition of 60 mg (0.14 mmol) of 2,2'-bis[2-(1-ethylbenzimidazol-2yl)]biphenyl the mixture was warmed. Upon cooling, a bright-blue crystalline solid precipitated. The precipitate was collected by filtration and was then redissolved in 5 mL of warm nitromethane. The solution was filtered and upon standing yielded bright-blue x-ray quality prisms. The following crystallographic data and FIGURE illustrates the crystal structure of Ni(diEtBBIL)Cl$_2$.

The x-ray crystallographic data for the composition is as follows:

FW=572.16 g/mol
Space group=P2$_1$2$_1$2$_1$
a=9.854(1) Å
b=16.695(2) Å
c=16.844(2) Å
V=2771.0(5) Å$^3$
Z=4
R=0.0469, wR$^2$=0.0510

[Note: Bond lengths are in Angstroms while bond angles are in degrees.]

| Ni(1)—N(3) | 1.998(8) | N(3)—Ni(1)—N(1) | 111.1(3) | N(3)—Ni(1)—Cl(1) | 111.5(2) |
| Ni(1)—Cl(1) | 2.226(2) | N(1)—Ni(1)—Cl(1) | 101.1(2) | N(3)—Ni(1)—Cl(2) | 102.1(2) |
| Ni(1)—N(1) | 2.008(7) | N(1)—Ni(1)—Cl(2) | 107.6(2) | Cl(1)—Ni(1)—Cl(2) | 123.41(11) |
| Ni(1)—Cl(2) | 2.233(3) | | | | |

Example 3
Preparation of ±2,2'-bis[2-(1-ethylbenzimidazol-2yl]biphenyl]nickel(II) dichloride (a.k.a., "Ni(diEtBBIL)Cl$_2$")

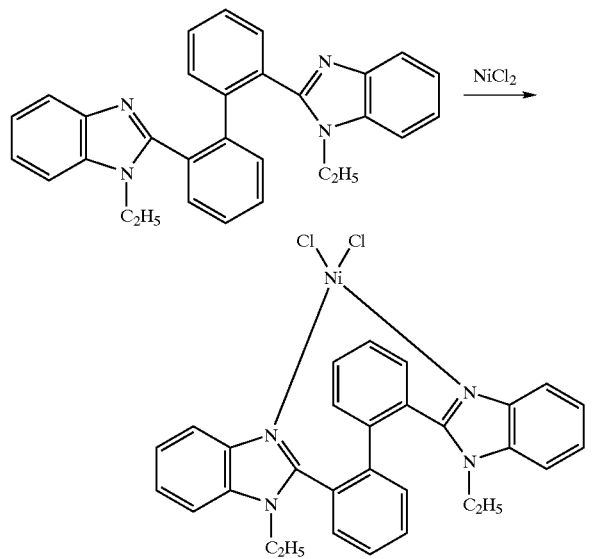

Example 4
Preparation of [1,1'bis(1-methylbenzimidazol-2yl)1=methoxymethane]nickel(II) dibromide (a.k.a., Ni(HBBIOMe)Br$_2$)

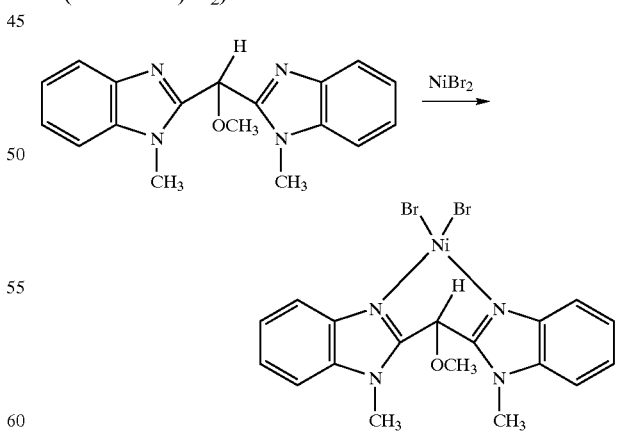

A 72 mg (0.36 mmol) quantity of NiBr$_2$ was added to a 20 mL solution of 1 to 1 acetone:methanol containing 200 mg (0.65 mmol) of [1,1'bis(1-methylbenzimidazol-2yl) 1" methoxymethane]__(HBBIMOMe) to give a pale violet solution upon mixing. After standing overnight, pale-violet crystals formed. These were collected by filtration and were dried under high vacuum. $C_{18}H_{18}Br_2N_4NiO$, FW=524.87.

II. Oligomerization

Example 5

Ethylene Oligomerization Using Ni(tributylBBIM)Cl$_2$

In an argon glovebox a toluene slurry was prepared in a 50 ml Parr glass liner by suspending Ni(tributBBIM)Cl$_2$ (FW 546.22) (8.3 mg, $1.52 \times 10^{-2}$ mmoles) (product of Example 2) in 7.95 g toluene followed by activation with 2.04 mL of 30% MAO (Al/Ni=695) to obtain a dark suspension. In the glovebox, the glass liner was placed into the Parr reactor. The reactor was transferred to a hood and then pressurized with 500 psig of ethylene. The solution was stirred (stirring rate 500 RPM) at 25° C. for 12 minutes. During the reaction the pressure dropped to almost zero psig. The reaction mixture was cooled and unreacted ethylene was vented to obtain 2.8 g of product. The product was analyzed by gas chromatography-mass spectrometry. GC analysis of the product indicated peaks due to butenes (88%) and hexenes (12%). No peaks corresponding to higher olefins were observed. Catalyst productivity was about 32900 moles ethylene reacted/moles of Ni catalyst per hour.

Example 6

Ethylene Oligomerization Using Catalyst Ni(tributylBBIM)Cl$_2$

In an argon glovebox a toluene slurry was prepared in a 50 ml Parr glass liner by suspending Ni(tributBBIM)Cl$_2$ (FW 546.22) (8.3 mg, $1.52 \times 10^{-2}$ mmoles) (product of Example 2) in 8.17 g toluene followed by activation with 2.05 mL of 30% MAO (Al/Ni=698) to obtain a dark suspension. In the glovebox, the glass liner was placed into the Parr reactor. The reactor was transferred to a hood and then pressurized with 500 psig of ethylene. The solution was stirred (stirring rate 500 RPM) at 25° C. for 30 minutes. During the reaction, the pressure dropped to almost zero psig. The reaction mixture was cooled and unreacted ethylene was vented to obtain 2.0 g of product. The product was analyzed by gas chromatography-mass spectrometry. GC analysis of the product indicated peaks due to butenes (89%) and hexenes (11%). No peaks corresponding to higher olefins were observed. Catalyst productivity was about 9400 moles ethylene reacted/moles of Ni catalyst per hour.

Example 7

Ethylene Oligomerization Using Catalyst Ni(diEtBBIL)Cl$_2$

In an Argon glovebox a toluene slurry was prepared in a 50 ml Parr glass liner by suspending Ni(diEtBBIL)Cl$_2$ (FW 572.16) (8.7 mg, $1.52 \times 10^{-2}$ mmoles) (product of Example 3) in 8.00 g toluene followed by activation with 2.00 mL of 30% MAO (Al/Ni=681) to obtain a dark suspension. In the glovebox, the glass liner was placed into the Parr reactor. The reactor was transferred to a hood and then pressurized with 500 psig of ethylene. The solution was stirred (stirring rate 500 RPM) at 25° C. for 10 minutes, then the solution was heated to 80° C. and stirred for total of 70 minutes. During the reaction, the pressure dropped to less than 50 psig. The reaction mixture was cooled and unreacted ethylene was vented to obtain 1.9 g of product. The product was analyzed by gas chromatography-mass spectrometry. GC analysis of the product indicated peaks due to butenes (92%) and hexenes (8%). No peaks corresponding to higher olefins were observed. Catalyst productivity was about 3825 moles ethylene reacted/moles of Ni catalyst per hour.

Example 8

Ethylene Oligomerization Using Catalyst Ni(diEtBBIL)Cl$_2$

In an argon glovebox a toluene slurry was prepared in a 50 ml Parr glass liner by suspending Ni(diEtBBIL)Cl$_2$ (FW 572.16) (8.3 mg, $1.45 \times 10^{-2}$ mmoles) (product of Example 3) in 8.00 g toluene followed by activation with 2.00 mL of 30% MAO (Al/Ni=713) to obtain a dark suspension. In the glovebox, the glass liner was placed into the Parr reactor. The reactor was transferred to a hood and then pressurized with 500 psig of ethylene. The solution was stirred (stirring rate 500 RPM) at 25° C. for 30 minutes. During the reaction, the pressure dropped to less than 50 psig. The reaction mixture was cooled and unreacted ethylene was vented to obtain 1.8 g of product. The product was analyzed by gas chromatography-mass spectrometry. GC analysis of the product indicated peaks due to butenes (95%) and hexenes (5%). No peaks corresponding to higher olefins were observed. Catalyst productivity was about 8860 moles ethylene reacted/moles of Ni catalyst per hour.

Example 9

Ethylene Oligomerization Using Catalyst Ni(HBBIOMe)Br$_2$

In an argon glovebox a toluene slurry was prepared in a 50 ml Parr glass liner by suspending Ni(HBBIOMe)Br$_2$ (FW 524.87) (8.5 mg, $1.52 \times 10^{-2}$ mmoles) (product of Example 4) in 8.00 g toluene followed by activation with 2.00 mL of 30% MAO (Al/Ni=680) to obtain a dark suspension. In the glovebox, the glass liner was placed into the Parr reactor. The reactor was transferred to a hood and then pressurized with 500 psig of ethylene. The solution was stirred (stirring rate 500 RPM) at 25° C. for 27 minutes. During the reaction, the pressure dropped to almost zero psig. The reaction mixture was cooled and unreacted ethylene was vented to obtain 2.3 g of product. The product was analyzed by gas chromatography-mass spectrometry. GC analysis of the product indicated peaks due to butenes (85%) and hexenes (15%). No peaks corresponding to higher olefins were observed. Catalyst productivity was about 11980 moles ethylene reacted/moles of Ni catalyst per hour.

Example 10

Gas Phase Ethylene Oligomerization Using Catalyst Ni(tributylBBIM)Cl$_2$

In an argon glovebox a toluene slurry was prepared in a 50 ml Parr glass liner by suspending Ni(tributBBIM)Cl$_2$ (FW 546.22) (8.3 mg, $1.52 \times 10^{-2}$ mmoles) (product of Example 2) in 8.01 g toluene followed by activation with 2.02 mL of 30% MAO (Al/Ni=688) to obtain a dark suspension. The solvent was removed under high vacuum and the residue or powder was loaded into 50 ml Parr reactor under nitrogen. The Parr reactor was pressurized with 350 psig of ethylene at 25° C. Within 3 hours, the ethylene pressure dropped from 350 psig to 80 psig. The reaction mixture was cooled and unreacted ethylene was vented to obtain 1.8 g of product. The product was analyzed by gas chromatography-mass spectrometry. GC analysis of the product indicated peaks due to butenes (70%) and hexenes (30%). No peaks corresponding to higher olefins were observed.

Example 11

Gas Phase Ethylene Oligomerization Using Catalyst Ni(tributylBBIM)Cl$_2$

In an argon glovebox a toluene slurry was prepared in a 50 ml Parr glass liner by suspending Ni(tributBBIM)Cl$_2$ (FW 546.22) (8.9 mg, $1.63 \times 10^{-2}$ mmoles) (product of Example 2) in 8.04 g toluene followed by activation with 2.01 mL of 30% MAO (Al/Ni=638) to obtain a dark suspension. The solvent was removed under high vacuum and powder was placed into a glass flitted vessel. The fritted vessel was placed into a 50 ml Parr glass liner, thus suspending the powdered catalyst. The Parr reactor was pressurized with 350 psig of ethylene at 25° C. Within 3 hours, the ethylene pressure dropped from 350 psig to 80 psig. The reaction mixture was cooled and unreacted ethylene was vented to obtain 1.26 g of product. The product was analyzed by gas chromatography-mass spectrometry. GC analysis of the product indicated peaks due to butenes (82.4%) and hexenes (17.6%). No peaks corresponding to higher olefins were observed.

Example 12

Ethylene Oligomerization Using Ni(tributylBBIM)Cl$_2$

In an Argon glovebox a toluene slurry was prepared in a 50 ml Parr glass liner by suspending Ni(tributBBIM)Cl$_2$ (FW 546.22) (8.9 mg, 1.63×10$^{-2}$ mmoles) (product of Example 2) in 8.06 g toluene followed by activation with 2.05 mL of 30% MAO (Al/Ni=650) to obtain a dark suspension. In the glovebox, the glass liner was placed into the Parr reactor. The reactor was transferred to a hood and then pressurized with 500 psig of ethylene. The solution was stirred (stirring rate 500 RPM) at 25° C. for 10 minutes. During the reaction, the pressure dropped to 200 psig. The Parr reactor was repressurized with ethylene to 500 psig and the solution was stirred at 25° C. for 12 minutes. During this period, pressure dropped again to 200 psig. The repressurization and ethylene reaction were continued seven additional times. The catalyst was still active. Finally, the reaction mixture was cooled and unreacted ethylene was vented to obtain 8.9 g of product. The product was analyzed by gas chromatography-mass spectrometry. GC analysis of the product indicated peaks due to butenes and hexenes.

Example 13

Ethylene Oligomerization Using Supported Catalyst

In a round bottom flask Ni(tributBBIM)Cl$_2$ (FW 546.22) (19.0 mg, 3.5×10$^{-2}$ mmoles) (product of Example 2) was dissolved into methylene chloride (16 mL) and stirred for 15 minutes. To the purplish solution MAO (30 wt % in toluene) was slowly added to give a greenish colored solution. After 30 minutes, silica (Grace-Davidson™ Grade 62 dehydrated) (0.5 gm) was added and stirring was continued for 18 hours. The flask was heated to 50° C. under vacuum (0.05 mm Hg) for 6 hours to give a dark solid. The supported catalyst (1.5472 gm) was placed into a fritted vessel. The fritted vessel was placed into a 50 ml Parr glass liner, thus suspending the supported catalyst. The Parr reactor was sealed then pressurized to 500 psig with ethylene. The reaction was run for 24 hours at room temperature. The pressure dropped from 500 psi to 300 psi. The reaction mixture was cooled and unreacted ethylene was vented to obtain 1.2 g of product. The product was analyzed by gas chromatography-mass spectrometry. GC analysis of the product indicated peaks due to butenes (64%) and hexenes (36%). No peaks corresponding to higher olefins were observed.

The foregoing examples clearly demonstrate that the novel composition of the instant invention can be used as an effective oligomerization catalyst to make α-olefins. More specifically, the examples show how olefinic monomers such as ethylene are readily oligomerized to selectively form short chain α-olefins such as butenes and hexenes. Additionally, the examples show that the catalyst can also be supported and such supported catalyst may also be used in oligomerization processes. Furthermore, the examples demonstrate that the invention can be used with or without solvent (i.e., gas phase oligomerization). The oligomerization can be run in batch, continuous, or reactive distillation modes. Most importantly, the invention provides a novel organometallic catalyst and oligomerization method which produces linear α-olefins with a high degree of selectivity and does not produce significant polymer co-product. These features overcome the disadvantages of the current organometallic technology discussed above in the background section. As a final note, experimentation has also shown that the invention is truly catalytic as the same catalyst can be used repeatedly to make α-olefins. More specifically, the catalysts used in the aforementioned examples retain their catalytic activity even after numerous runs (i.e., more than about six).

What is claimed is:

1. A composition comprising:

(a) a metal complex having the formula LMX(X')$_n$ wherein n equals 0 or 1; X and X' are independently selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolates, carbon monoxide, cyanate and olefins; M is selected from the group consisting of nickel, palladium and platinum; and L is a nitrogen-containing bidentate ligand with more than two nitrogen atoms; and (b) an activating cocatalyst.

2. The composition according to claim 1 wherein L is selected from the group consisting of 1,1'-bis(1-methylbenzimidazol-2-yl)-1"-methoxymethane, 1,1'-bis(1-butylbenzimidazol-2-yl) pentane, and 2,2'-bis(2-(1-ethylbenzimidazol-2-yl))biphenyl.

3. The composition according to claim 1 wherein X and X' are independently selected from the group consisting of chlorine and bromine.

4. The composition according to claim 3 wherein said X equals X'.

5. The composition according to claim 1 wherein L has the formula A(ZR*)$_m$A' or AA' wherein A and A' are independently selected from the group consisting of:

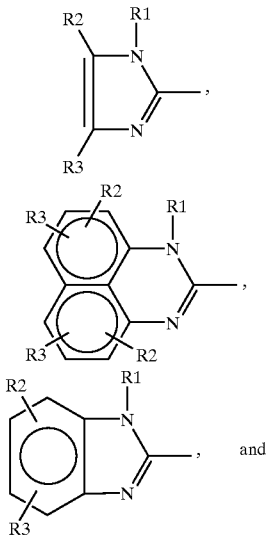

-continued

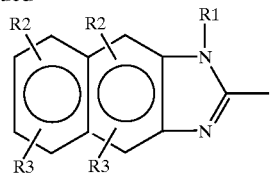

wherein

R1 is independently selected from the group consisting of hydrogen, $C_1$ through $C_{12}$ alkyl, $C_3$ through $C_{12}$ cycloalkyl, aryl, and trifluoroethyl;

R2 and R3 are independently selected from the group consisting of hydrogen, $C_1$ through $C_{12}$ alkyl, $C_3$ through $C_{12}$ cycloalkyl, $C_1$ through $C_{12}$ alkoxy, F, Cl, $SO_3$, $C_1$ through $C_{12}$ perfluoroalkyl, trimethylsilyl, and $N(CH_3)_2$;

Z is carbon;

R* is independently selected from the group consisting of hydrogen, $C_1$ through $C_{12}$ alkyl, $C_3$ through $C_{12}$ cyclo alkyl, aryl, $C_1$ through $C_{12}$ alkoxy, F, Cl, $SO_3$, $C_1$ through $C_{12}$ perfluoroalkyl, trimethylsilyl, and $N(CH_3)_2$;

m is 1 to 22.

6. The composition of claim 1 wherein said activating cocatalyst is selected from the group consisting of alkylalumoxanes, aluminum alkyls, aluminum halides, alkyl aluminum halides, Lewis acids, alkylating agents, and mixtures thereof.

7. The composition of claim 1 wherein said activating cocatalyst is methyl alumoxane.

8. The composition of claim 1 wherein the ratio of the metal complex to the activating cocatalyst is from $1:10^{-2}$ to $1:10^6$.

9. The composition of claim 1 wherein the composition is supported.

10. The composition of claim 9 wherein the composition is supported by silica.

11. A method for producing α-olefins comprising contacting an olefinic monomer or monomers under oligomerization conditions with a catalyst composition comprising the reaction product of:

(a) a metal complex having the formula $LMX(X')_n$ wherein n equals 0 or 1; X and X' are independently selected from the group consisting of halides, hydride, triflate, acetates, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolates, carbon monoxide, cyanate and olefins; M is selected from the group consisting of nickel, palladium and platinum; and L is a nitrogen-containing bidentate ligand with more than two nitrogen atoms; and (b) an activating cocatalyst.

12. The method according to claim 11 wherein L has the formula $A(ZR^*)_mA'$ or AA' wherein A and A' are independently selected from the group consisting of:

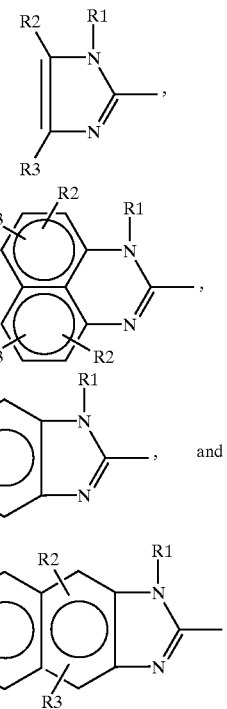

wherein

R1 is independently selected from the group consisting of hydrogen, $C_1$ through $C_{12}$ alkyl, $C_3$ through $C_{12}$ cycloalkyl, aryl, and trifluoroethyl;

R2 and R3 are independently selected from the group consisting of hydrogen, $C_1$ through $C_{12}$ alkyl, $C_3$ through $C_{12}$ cycloalkyl, $C_1$ through $C_{12}$ alkoxy, F, Cl, $SO_3$, $C_1$ through $C_{12}$ perfluoroalkyl, trimethylsilyl, and $N(CH_3)_2$;

Z is carbon;

R* is independently selected from the group consisting of hydrogen, $C_1$ through $C_{12}$ alkyl, $C_3$ through $C_{12}$ cyclo alkyl, aryl, $C_1$ through $C_{12}$ alkoxy, F, Cl $SO_3$, $C_1$ through $C_{12}$ perfluoroalkyl, trimethylsilyl, and $N(CH_3)_2$;

m is 1 to 22.

13. The method of claim 11 wherein the cocatalyst is selected from the group consisting of alkylalumoxanes, aluminum alkyls, aluminum halides, alkyl aluminum halides, Lewis acids other than any of the foregoing, alkylating agents and mixtures thereof.

14. The method of claim 11 wherein the cocatalyst is methyl alumoxane.

15. The method of claim 11 wherein the contacting is at a temperature in the range of from about 0 to 100° C. and at pressures of from about 15–2000 psig.

16. The method of claim 11 wherein the contacting is conducted in a solvent.

17. The method of claim 11 wherein the contacting is conducted neat.

18. The method of claim 11 wherein the contacting is conducted in a gas phase.

19. The method of claim 11 wherein said olefinic monomer is selected from the group consisting of ethylene, propylene, butene and mixtures thereof.

20. The method of claim 11 wherein said olefinic monomer is ethylene.

* * * * *